US00PP10433P

United States Patent [19]

Kientzler

[11] Patent Number: Plant 10,433

[45] Date of Patent: Jun. 2, 1998

[54] NEW GUINEA IMPATIENS PLANT 'KINOC'

[75] Inventor: Ludwig Kientzler, Gensingen, Germany

[73] Assignee: Paul Ecke Ranch, Inc., Encinitas, Calif.

[21] Appl. No.: 797,492

[22] Filed: Feb. 7, 1997

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—C. A. Whealy

[57] ABSTRACT

A new and distinct cultivar of New Guinea Impatiens plant named 'Kinoc', and to be marketed under the name 'Noctua', characterized by its magenta-colored flowers; freely flowering habit; outwardly spreading, mounded and rounded growth habit; freely branching plant habit; and dark green, glossy, non-variegated foliage.

2 Drawing Sheets

1

The present invention relates to a new and distinct cultivar of New Guinea Impatiens plant, botanically known a *Impatiens hawkeri,* which is to be internationally registered as 'Kinoc'. It is anticipated that the plant will be marketed under the synonym 'Noctua'. Hereinafter the disclosed plant will be referred to as 'Noctua'.

The new cultivar is a product of a planned breeding program conducted by the inventor in Gensingen, Germany. The objective of the breeding program was to develop new varieties that have a uniform plant habit, attractive flower colors, good flower form and numerous flowers per plant.

The new cultivar originated from a cross made by the inventor of a proprietary seedling selection identified as P229 as the male, or pollen parent, with the proprietary seedling selection identified as K523 as the female, or seed patent. The cultivar Noctua was discovered and selected by the inventor as a flowering plant within the progeny of the stated cross in a controlled environment in Gensingen, Germany. Asexual reproduction of the new cultivar by terminal cuttings taken at Gensingen, Germany, has shown that the unique features of this new Impatiens are stable and reproduced true to type in successive generations of asexual reproduction.

The following traits have been repeatedly observed and are determined to be the unique characteristics of 'Noctua'. These characteristics in combination distinguish 'Noctua' as a new and distinct cultivar:

1. Magenta-colored flowers.
2. Freely flowering.
3. Outwardly spreading, rounded and mounded growth habit.
4. Freely branching plant habit.
5. Dark green, glossy, non-variegated foliage.

The new New Guinea Impatiens is similar in flower color to the New Guinea Impatiens cultivar Anguilla (U.S. Plant patent applied for). However in side-by-side comparisons in Encinitas, Calif., under commercial practice, plants of the new New Guinea Impatiens differed from plants of the cultivar 'Anguilla' in the following characteristics:

1. Plants of the new New Guinea Impatiens more outwardly spreading and more rounded and mounded than plants of the cultivar 'Anguilla'.

2. Plants of the new New Guinea Impatiens are shorter than plants of the cultivar 'Anguilla'.

3. The adaxial surface of mature leaves of plants of the new New Guinea Impatiens is dark green in color whereas the adaxial surface of mature leaves of plants of the cultivar 'Anguilla' is dark red in color.

2

4. Plants of the new New Guinea Impatiens are more freely flowering than plants of the cultivar 'Anguilla'. 5. Petal color of plants of the new New Guinea Impatiens does not fade with age whereas petal color of plants of the cultivar 'Anguilla' fades with age.

6. Flower spurs of plants of the new New Guinea Impatiens are shorter than flower spurs of plants of the cultivar 'Anguilla'.)

A detailed comparison of plants of the new New Guinea Impatiens and the cultivar 'Anguilla' appears in Chart A at the end of the specification.

The accompanying colored photographs illustrate the overall appearance of the new cultivar, showing the colors as true as it is reasonably possible to obtain in colored reproductions of this type.

The first photograph comprises a top perspective view of a typical plant of 'Noctua'.

The second photograph comprises a close-up view of typical flowers and leaves of the varieties 'Anguilla' (top of photo) and Noctua (bottom of photo).

The flower and foliage colors in the photographs may differ from the actual colors due to light reflectance.

The cultivar 'Noctua' has not been observed under all possible environmental conditions. The phenotype may vary somewhat with variations in environment such as temperature and light intensity, without, however, any variance in genotype. The following observations, measurements and comparisons describe plants grown 10-cm pots in Encinitas, Calif., under commercial practice in a fiberglass-covered greenhouse with day temperatures ranging from 23 to 29C. and night temperatures ranging from 16 to 18C. with light levels averaging 3,000 footcandles.

In the following description, color references are made to The Royal Horticultural Society Colour Chart except where general terms of ordinary dictionary significance are used.

Classification:

*Botanical.*—*Impatiens hawkeri.*

*Commercial.*—New Guinea Impatiens 'Kinoc', sold under 'Noctua'.

Parentage:

*Male parent.*—Proprietary seedling selection P229.

*Female parent.*—Proprietary seedling selection K523.

Propagation:

*Type cutting.*—Terminal cuttings.

*Time to initiate roots.*—About 15 days with 21C. soil temperature.

Plant description:

*Plant form.*—Outwardly spreading, rounded and mounded.

*Growth habit.*—Moderately vigorous to vigorous. Freely branching, dense and bushy. Suitable for 10 to 25-cm containers.

*Plant size.*—Height: About 16 cm. Width or spread: About 26 cm.

*Lateral branches.*—Quantity: Six to eight. Size: Length: About 10 cm. Diameter: About 8 mm. Internode length: About 5 cm. Color: 59A.

*Foliage description.*—Leaves simple, generally symmetrical, abundant, opposite or in whorls of three, horizontal to plant and flat in aspect. Size, largest leaves: Length: About 12 cm. Width: About 4 cm. Shape: Ovate with acuminate apex, attenuate base and ciliate margin. Texture: Smooth, glossy. Color: Young foliage, upper surface: 137A. Young foliage, lower surface: 147B. Fully expanded foliage, upper surface: 147A. Fully expanded foliage, lower surface: 147B. Venation, upper surface: 59B. Venation, lower surface: 59A. Petiole: Size: Length: About 2.75 cm. Diameter: About 3 mm. Color: 59B.

Flower description:

*Flower type and habit.*—Magenta-colored flowers. Freely and continuously flowering. Flowers arise from leaf axils. Usually ten to twelve flowers per lateral branch. Flowers positioned above the foliage and face upward or outward. Flowers slightly cupped to flat and rounded to rectangular. Flowers persistent.

*Flowering season.*—Year-round under greenhouse conditions. In the garden, flowering is continuous from spring until fall.

*Flower size.*—Length: About 6.5 cm. Width: About 6 cm. Depth: 3 mm.

*Flower buds.*—Size: Length: About 2.2 cm. Diameter: About 1.6 cm. Shape: Ovoid. Color: Slightly redder than 57A.

*Petals.*—Quantity: Five. Size (largest petals): Length: Top petal: About 2.8 cm. Middle petals: About 2.6 cm. Bottom petals: About 3.7 cm. Width: Top petal: About 4 cm. Middle petals: About 2.8 cm. Bottom petals: About 3.8 cm. Shape: Cordate with emarginate apex, cuneate or obtuse base and entire margin. Texture: Velvety, smooth. Color: When opening, upper surface: Iridescent, brighter and darker than 57A. When opening, lower surface: Iridescent, 58B with 57A at edges. Fully opened, upper surface: Iridescent, brighter and darker than 57A with 66A centers. Fully opened, lower surface: Iridescent, slightly darker than 58B. Fading to: Color does not fade.

*Spur.*—Length: About 4.8 cm. Shape: Narrow and curved. Color: 59A.

*Peduncles.*—Length: 5.5 to 6 cm. Angle: Erect and outward. Strength: Strong. Color: 59A.

*Reproductive organs.*—Androecium: Stamen number: Five, anthers fused, filaments free. Anther shape: Obovate. Anther size: 6 by 4 mm. Anther color: Light cream. Amount of pollen: Moderate. Pollen color: Off-white/cream. Gynoecium: Five-loculate fused. Gynoecium length: About 5 mm. Gynoecium color: 146B.

Disease resistance:

Under commercial conditions, resistance nor susceptibility to pathogens has not been observed.

Seed development Seed production is not usually observed.

CHART A

| CHARACTERISTIC | 'NOCTUA' | 'ANGUILLA' |
|---|---|---|
| GROWTH HABIT | Outwardly spreading, rounded and mounded | Upright to slightly arching |
| PLANT HEIGHT | About 16 cm | About 18 cm |
| INTERNODE LENGTH | About 5 cm | About 4 cm |
| LEAF LENGTH | About 12 cm | About 10.5 cm |
| LEAF WIDTH | About 4 cm | About 4.5 cm |
| LEAF COLOR, MATURE, LOWER SURFACE | 147B | 59A |
| PETIOLE LENGTH | About 2.75 cm | About 3.75 cm |
| PETIOLE DIAMETER | About 3 mm | About 4 mm |
| QUANTITY OF FLOWERS PER LATERAL STEM | 10 to 12 | 8 to 10 |
| PETAL COLOR FADING | Color does not fade | Color fades with age |
| SPUR LENGTH | About 4.8 cm | About 5.2 cm |
| PEDUNCLE LENGTH | 5.5 to 6 cm | About 5 cm |
| PEDUNCLE COLOR | 59A | 60A |
| FLOWER BUD COLOR | Redder than 57A | Brighter than 61B |

It is claimed:

1. A new and distinct cultivar of New Guinea Impatiens plant, as illustrated and described.

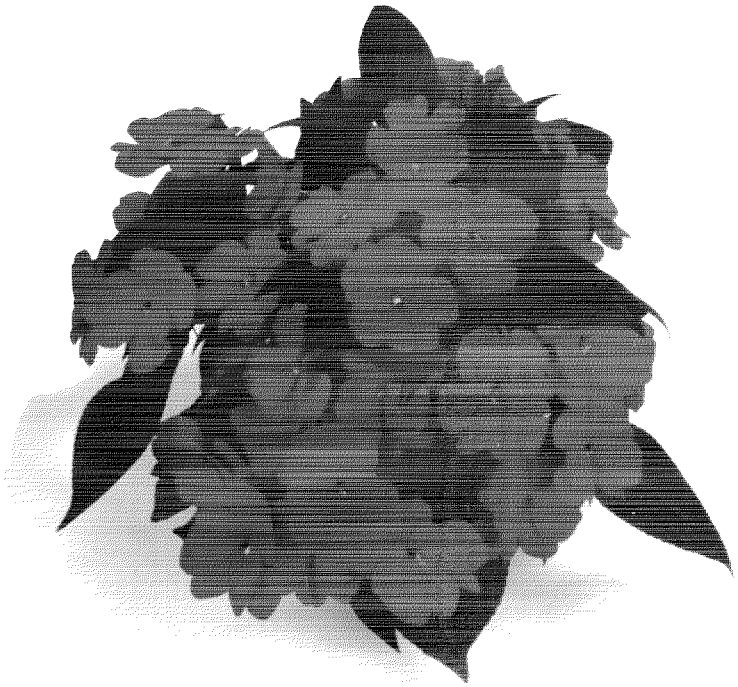

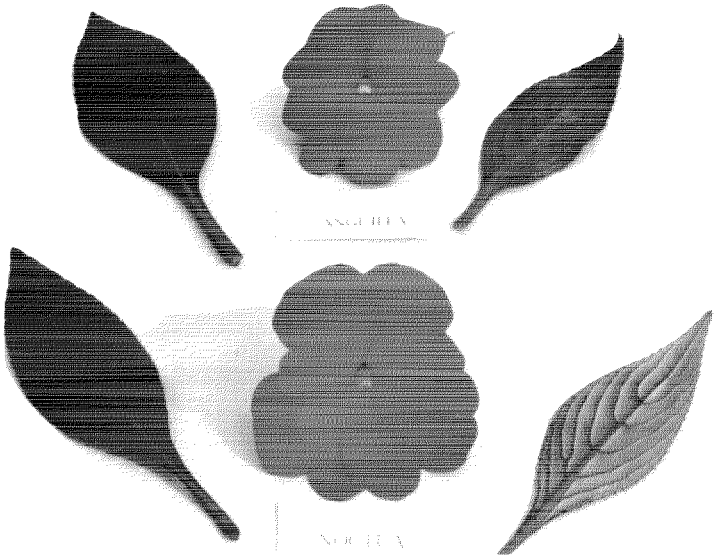

* * * * *